(12) United States Patent
Doleac et al.

(10) Patent No.: US 8,962,049 B2
(45) Date of Patent: *Feb. 24, 2015

(54) CAPSULE FOR PREPARING A NUTRITIONAL PRODUCT INCLUDING A FILTER AND METHOD

(75) Inventors: Frédéric Doleac, Vaux et Chantegrue (FR); Sophie Abraham, Malbuisson (FR); Yasmine Doudin, Vallorbe (CH); Yann Epars, Penthalaz (CH); Thierry Jean Robert Fabozzi, Geneva (CH); Heinz Wyss, Oberdiessbach (CH); Nicolas Bezet, Macon (FR); Lucio Scorrano, Yverdon-les-Bains (CH); Nihan Dogan, La Croix-sur-Lutry (CH); Alain Meier, Caneggio (CH)

(73) Assignee: Nestec S.A., Vevey (CH)

(*) Notice: Subject to any disclaimer, the term of this patent is extended or adjusted under 35 U.S.C. 154(b) by 351 days.
This patent is subject to a terminal disclaimer.

(21) Appl. No.: 13/319,041

(22) PCT Filed: May 4, 2010

(86) PCT No.: PCT/EP2010/056043
§ 371 (c)(1),
(2), (4) Date: Nov. 4, 2011

(87) PCT Pub. No.: WO2010/128051
PCT Pub. Date: Nov. 11, 2010

(65) Prior Publication Data
US 2012/0052164 A1 Mar. 1, 2012

(30) Foreign Application Priority Data

May 5, 2009 (EP) .................................. 09159373
Jun. 11, 2009 (EP) .................................. 09162485

(51) Int. Cl.
*A47J 31/06* (2006.01)
*B01D 63/00* (2006.01)
(Continued)

(52) U.S. Cl.
CPC ................ *A47J 31/44* (2013.01); *A47J 31/407* (2013.01); *A47J 36/2411* (2013.01);
(Continued)

(58) Field of Classification Search
USPC .......... 426/77, 78, 79, 115, 394; 99/295, 323, 99/301; 210/321.75, 289, 445, 455
See application file for complete search history.

(56) References Cited

U.S. PATENT DOCUMENTS 663,271 A * 12/1900 Hamilton ...................... 210/251
3,730,353 A * 5/1973 Trasen et al. .................. 210/455
(Continued)

FOREIGN PATENT DOCUMENTS

CN 2036061 U 4/1989
CN 2436167 Y 6/2001
(Continued)

OTHER PUBLICATIONS

Definition of "micro" and "nozzle." Webster's New World Dictionary, Third College Edition. Simon & Schuster 1988.*
(Continued)

*Primary Examiner* — Viren Thakur
(74) *Attorney, Agent, or Firm* — K&L Gates LLP

(57) ABSTRACT

Capsule and filter unit for the preparation of a nutritional product in a device adapted to supply liquid in the capsule. The capsule is constructed to have at least one compartment containing nutritional ingredients for the preparation of the nutritional product in combination with the supplied liquid, and a filter adapted for removing contaminants contained in the liquid. The filter is formed as a relatively rigid filter unit that includes a filter membrane and an outlet wall for supporting the filter membrane. The outlet wall has at least one liquid outlet communicating with the compartment.

15 Claims, 9 Drawing Sheets

(51) Int. Cl.
| | | |
|---|---|---|
| *B01D 27/08* | (2006.01) | |
| *A47J 31/44* | (2006.01) | |
| *A47J 31/40* | (2006.01) | |
| *A47J 36/24* | (2006.01) | |
| *B01D 63/08* | (2006.01) | |
| *B01D 65/00* | (2006.01) | |
| *B01D 69/10* | (2006.01) | |
| *B65D 85/804* | (2006.01) | |

(52) U.S. Cl.
CPC ............ *B01D 63/087* (2013.01); *B01D 65/00* (2013.01); *B01D 69/10* (2013.01); *B65D 85/8043* (2013.01); *B01D 2313/025* (2013.01); *B01D 2313/083* (2013.01); *B01D 2313/20* (2013.01); *B01D 2313/44* (2013.01)
USPC ............................... 426/77; 426/115; 99/295

(56) References Cited

U.S. PATENT DOCUMENTS

| | | | |
|---|---|---|---|
| 4,027,582 A * | 6/1977 | O'Connell | 99/306 |
| 4,136,202 A | 1/1979 | Favre | 426/77 |
| 4,500,426 A * | 2/1985 | Ishii et al. | 210/321.73 |
| 4,867,876 A * | 9/1989 | Kopf | 210/228 |
| 4,867,993 A * | 9/1989 | Nordskog | 426/77 |
| 5,011,555 A * | 4/1991 | Sager | 156/73.1 |
| 5,186,830 A * | 2/1993 | Rait | 210/232 |
| 5,510,027 A * | 4/1996 | Tejeda | 210/282 |
| 5,681,468 A | 10/1997 | Sawan et al. | |
| 6,103,116 A * | 8/2000 | Koslow et al. | 210/282 |
| 6,245,230 B1 * | 6/2001 | Ricci | 210/232 |
| 6,312,609 B1 * | 11/2001 | Solyanik et al. | 210/767 |
| 6,599,428 B1 * | 7/2003 | Douglas | 210/668 |
| 6,805,041 B2 * | 10/2004 | Colston et al. | 99/295 |
| 6,955,700 B2 | 10/2005 | Zia et al. | |
| 7,032,507 B2 * | 4/2006 | Cai | 99/323 |
| 2002/0059870 A1 * | 5/2002 | Walters Jr. et al. | 99/298 |
| 2004/0005384 A1 * | 1/2004 | Cai | 426/77 |
| 2004/0228955 A1 | 11/2004 | Denisart et al. | 426/590 |
| 2006/0236871 A1 * | 10/2006 | Ternite et al. | 99/295 |
| 2007/0000390 A1 * | 1/2007 | Albrecht | 99/279 |
| 2007/0144355 A1 * | 6/2007 | Denisart et al. | 99/275 |
| 2007/0148290 A1 | 6/2007 | Ternite et al. | 426/90 |
| 2007/0186784 A1 * | 8/2007 | Liverani et al. | 99/295 |
| 2007/0199888 A1 | 8/2007 | Japp et al. | 210/474 |
| 2007/0259073 A1 * | 11/2007 | Scarchilli et al. | 426/78 |
| 2008/0035550 A1 | 2/2008 | Fecondini et al. | |
| 2008/0257165 A1 * | 10/2008 | Bolzicco et al. | 99/295 |
| 2009/0004335 A1 | 1/2009 | MacMahon et al. | |
| 2009/0047389 A1 | 2/2009 | Jarisch et al. | 426/80 |
| 2009/0126578 A1 * | 5/2009 | Amann et al. | 99/295 |
| 2009/0155422 A1 | 6/2009 | Ozanne | 426/89 |
| 2010/0108541 A1 | 5/2010 | Roberto | 206/0.5 |
| 2012/0052159 A1 | 3/2012 | Doleac et al. | 426/79 |
| 2012/0052163 A1 | 3/2012 | Doleac et al. | 426/112 |

FOREIGN PATENT DOCUMENTS

| | | | | |
|---|---|---|---|---|
| CN | 1826071 | A | 8/2006 | |
| DE | 102005058336 | A1 | 6/2007 | |
| EP | 1364605 | A1 | 11/2003 | |
| EP | 1 574 452 | A2 | 9/2005 | |
| EP | 1 774 878 | A1 | 4/2007 | |
| EP | 1 826 148 | A1 | 8/2007 | |
| EP | 1500358 | B1 | 9/2007 | |
| EP | 1 980 501 | A1 | 10/2008 | |
| EP | 1 982 933 | A1 | 10/2008 | |
| EP | 2082670 | A1 | 7/2009 | |
| EP | 2 236 437 | A1 | 10/2010 | |
| EP | 2244593 | A1 | 11/2010 | |
| EP | 2244743 | A1 | 11/2010 | |
| EP | 2285256 | A1 | 2/2011 | |
| EP | 2299851 | A1 | 3/2011 | |
| EP | 2194824 | B1 | 9/2011 | |
| EP | 2230973 | B1 | 10/2011 | |
| EP | 2427065 | B1 | 12/2012 | |
| JP | 06-315349 | A | 11/1994 | |
| WO | WO 01/51166 | A1 | 7/2001 | |
| WO | WO 2005/080223 | A1 | 9/2005 | |
| WO | WO 2006/043108 | A1 * | 4/2006 | |
| WO | WO 2006/077259 | A1 | 7/2006 | |
| WO | WO 2007/125337 | A1 * | 11/2007 | |
| WO | WO 2008/012314 | A1 | 1/2008 | |
| WO | WO 2008/078989 | A1 * | 7/2008 | B65D 85/804 |
| WO | WO 2008/132571 | A1 | 11/2008 | |
| WO | WO 2008/148834 | A1 | 12/2008 | |
| WO | WO2008146115 | A1 | 12/2008 | |
| WO | WO2008147195 | A1 | 12/2008 | |
| WO | WO2009027131 | A1 | 3/2009 | |
| WO | WO 2009/092629 | A1 | 7/2009 | |
| WO | WO2009092628 | A1 | 7/2009 | |
| WO | WO2009092774 | A1 | 7/2009 | |
| WO | WO 2009/115475 | A1 | 9/2009 | |
| WO | WO2009135177 | A1 | 11/2009 | |
| WO | WO2010003878 | A1 | 1/2010 | |
| WO | WO2010128028 | A1 | 11/2010 | |

OTHER PUBLICATIONS

"USDA National Nutrient Database" Apr. 3, 2009 http://web.archive.org/web/20090104004513/http://www.ars.usda.gov/Services/docs.htm?docid=10091 http://web.archive.org/web/20090403101002/http://www.nal.usda.gov/fnic/foodcomp/Data/SR18/reports/sr18fg14.pdf.*
Definition of "central" and "port." Websters New World Dictionary 3rd College Edition, 1988 Simon & Schuster.*
International Search Report, PCT/EP2010/056043, mailed Jul. 12, 2010.
Non Final Office Action, U.S. Appl. No. 13/318,981, dated May 24, 2013.
International Search Report, EP2010056005, mailed Jul. 12, 2010.
International Search Report, EP2010056002, mailed Jul. 12, 2010.

* cited by examiner

CAPSULE FOR PREPARING A NUTRITIONAL PRODUCT INCLUDING A FILTER AND METHOD This application is a 371 filing of International Patent Application PCT/EP2010/056043 filed May 4, 2010.

BACKGROUND

The present invention relates to a capsule for hygienically preparing a nutritional product containing nutritional ingredients by mixing the ingredients with a liquid; the capsule containing a filter filtering the liquid supplied in the capsule for removing undesired components contained in the liquid. The invention more particularly relates to a capsule for insertion in a device for supplying liquid in the capsule for preparing a nutritional product by mixing with the nutritional ingredients such as an infant formula, growing-up formula or adult nutrition formula. The invention also relates to a method using such capsule.

Nutritional compositions can be, for instance, infant formulas or also nutritional liquids for toddlers, invalids, elderly people, persons having nutritional deficiencies or athletes. These compositions are prepared from ingredients contained in a capsule by addition of a liquid such as water. The liquid may contain undesired contaminants such as micro-organisms and/or solid particles (e.g., dust, minerals, organic residues, etc.). These undesired contaminants should be removed from the liquid before the liquid is mixed with the ingredients to ensure an hygienic and safe preparation of the composition.

Therefore, there is a need for a capsule which enables preparation of nutritional composition for instance an infant formula or other food compositions in a convenient and safe manner.

WO2006/077259 discloses a method for preparing a single serving of a nutritional composition comprising introducing liquid such as water into a cartridge containing a unit dose of the composition in concentrated form. Thereby, the water is treated prior to the introduction into the cartridge in order to remove pathogens from the water. This treatment may be for instance a pre-heating, a filtering or an irradiation of the water with ultra-violet light.

WO 2008/012314 relates to a device which teaches the principle of treating water by means of a filter used for the preparation of nutritional compositions from a capsule inserted in a dispenser.

WO2009/115475 relates to a capsule for the preparation of a liquid comprising a puncturable delivery wall.

A capsule with an integrated antimicrobial filter has been described in WO 2009/092629 and No. 09156782.6 filed on 31 Mar. 2009.

The antimicrobial filter is preferably a thin microporous membrane which requires extremely precautionary measures when handling and positioning in the capsule during manufacturing. Handling of the filter itself should be controlled in order to avoid beforehand contamination. Furthermore, a reliable positioning and connection of the filter in the capsule must be assured to avoid any filtering defect during beverage preparation. Therefore, handling of the filter should be facilitated by a solution which is adapted to mass production whereby ensuring elevated hygiene and quality standards.

Furthermore, there is also a need for optimizing the use of packaging (i.e., non-food) materials in the capsule without detriment to the resistance of the capsule to the positive liquid pressure reigning in the capsule and preferably to provide a more environmentally friendly and cost effective product.

Another requirement is to ensure the release of the dedicated amount of the nutritional composition contained in the capsule to ensure a complete feed for each capsule, e.g., to the baby or child. No significant amount of nutritional liquid should be left in the capsule, most preferably, the capsule should be emptied from any liquid and solids. For this, the filter in the capsule can create a too high resistance to the pressurized gas (e.g., air) injected in the capsule during the emptying operation. As a result, the pressure of gas can be insufficient to properly empty the capsule or a too high pressure of gas is required which has an impact on the complexity and cost of the system.

Another requirement is to ensure that there is no contact during emptying of the capsule, i.e., between the gas opening device for the gas purge and contaminated liquid, e.g., nutritional ingredients or liquid, which would otherwise require systematic cleaning and so a clean-in-place system which would render the device more complex.

Another requirement is to ensure that the filter can support the deformation under the pressure of liquid supplied in the capsule, in particular, the pressure at the upstream surface of filter.

SUMMARY OF THE INVENTION

The present invention now overcomes one or more of the above-referenced problems by providing a capsule and a filter unit for the capsule as set forth herein.

In particular, the present invention relates to a capsule for the preparation of a nutritional product in a device adapted to supply liquid in the capsule, said capsule comprising:

at least one compartment containing nutritional ingredients for the preparation of the nutritional product in combination with the supplied liquid, a filter adapted for removing contaminants contained in the liquid, characterized in that the filter is formed as a filter unit which comprises a filter membrane and an outlet wall for supporting the filter membrane; the outlet wall comprising at least one liquid outlet communicating with the compartment.

Preferably, the liquid outlet is positioned axially offset relative to the filtering surface of the filter membrane.

Preferably, the filter unit is positioned axially offset relative to the compartment.

Preferably, the capsule has a body delimiting a compartment for the ingredients and a filter-receiving seat for the filter unit. The filter-receiving seat is preferably located on a side of the compartment.

Preferably, the filter unit is relatively rigid.

In a preferred mode, the filter unit comprises relatively rigid casing encasing the filter membrane. As a result, the production of the capsule is facilitated and more hygienic since contact with the filter membrane can be avoided.

The casing is preferably pressure resistant and handleable, By "handleable", it is meant here that the filter unit forms an assembly that can be handled or manipulated, such during manufacturing of the capsule, while maintaining the filter membrane protected from external contact and mechanical constraints by the casing.

Preferably, the filter membrane of the unit is a microporous membrane.

More particularly, the filter unit comprises an inlet wall forming with the outlet wall, an inner compartment in which the filter is inserted and further liquid imperviously sealed at its circumference to the casing.

Such an encasing structure ensures an appropriate protection of the filter membrane both when the capsule is produced and during preparation of the nutritional liquid composition.

The casing also at least partially bears the pressing and sealing forces exerted by the liquid supply device onto the capsule thereby relieving the effort on the filter membrane itself to avoid its rupture or damage.

Preferably, the casing is formed of two half-casings which are welded together. The filter can be pinched and/or welded at its circumference by the casing, e.g., the two half-casings assembling together. The half-casings can be plastic elements assembling together by clipping and/or ultrasonic welding. These elements are sufficiently rigid to resist bending under the pressure of liquid injected in the capsule. These elements can be made of a foodgrade polymer such PP, PA, PE, PA/PP, PVC, PS, PEEK, PLA, starch-based material or metal such as aluminium and combinations thereof.

Preferably, the outlet wall preferably comprises a structure in relief, such as a plurality of ridges/studs, for reserving space for the filtered liquid. In a particular mode, the microporous membrane can be supported at its downstream outlet surface by said structure in relief protruding inwards the inner compartment of the casing and distributed across the surface of the microporous membrane. This relief structure ensures a minimal deflection of the filter membrane under the pressure of liquid and also enables collection of the liquid at the downstream side of filter to an outlet of the casing to be supplied in the compartment. In another mode, the structure in relief supports the top membrane of the capsule to avoid it collapsing and blocking the flow of liquid at the outlet wall of the filter unit.

The inlet wall of the casing comprises at least one inlet for liquid. The inlet comprises at least one perforation-resistant deflector traversing the axis of the inlet port for preventing perforation of the microporous membrane by a perforator foreign to the capsule. The deflector can be a transversal portion provided in the inlet opening of the casing and made integral with the inlet wall of the casing. The deflector may take various shapes and sizes (e.g., width and thickness).

The filter unit preferably has a cross section, taken along the transversal plane of the capsule, which is smaller than the cross section of the compartment containing the ingredients. Most preferably, the cross section of the filter unit is at least two times smaller than the cross section of the compartment. One advantage is to reduce the deflection of the filter at its centre. Another advantage concerns the lowering of the amount of packaging material to form the filter unit and consequently reducing its impact on environment and furthermore lowering its production cost.

The capsule can also comprise a body, for instance, forming a cup for receiving the ingredients (e.g. infant formula). The body delimits the first compartment and a filter-receiving seat placed upstream of the compartment for lodging the filter unit. The filter receiving seat enables an easy placement of the filter unit during assembly of the capsule on the production line. The number of elements of the capsule can also be significantly reduced. The body may be formed in moulded plastic such as by injection-moulding or thermoforming.

The filter-receiving seat can be so placed transversally in an offcentred position relative to the first compartment. By offcentring the filter-receiving seat, the filter unit can be displaced on a side of the capsule relative to the compartment to allow a connection with the liquid supply device more efficient and less prone to deformation by the pressure of liquid.

In a preferred capsule's design, the filter receiving seat extends by a flange-like rim which merges continuously with the flange-like rim of the compartment.

More particularly, the filter unit comprises an outlet nozzle extending from the offcentred filter-receiving seat towards and above the first compartment. The outlet nozzle comprises one or at least a limited number of small-diameter outlets for providing a high-momentum jet of liquid in the compartment. Preferably, the nozzle comprises a single outlet having a diameter of less 1.0 mm, most preferably between 0.2 and 0.7 mm. The outlet is capable of providing a jet of liquid with a flow velocity comprised between 1 and 20 msec. The jet created by the nozzle produces a turbulent flow in the compartment which is effective for dissolving and/or dispersing all the ingredients in the liquid.

An openable gas inlet is also placed in the capsule to bypass the filter membrane and provides communication between the exterior of the capsule and the interior of the first compartment. More preferably, the openable gas inlet is formed in the filter unit, e.g., through the inlet wall, and communicates with the outlet nozzle. The gas inlet enables introduction of gas under pressure for emptying the capsule from liquid and so ensuring that the full content of the capsule is well delivered from the capsule. The gas inlet can be opened by piercing or breaking a part of the capsule. When the gas inlet is placed in communication with the filtered side of the filter unit, i.e., conduit leading to the nozzle, it is assured that the opening member pertaining to the liquid supply device for opening the gas inlet comes in contact only with filtered liquid.

In particular, a common top membrane is sealed onto the compartment and filter unit. The membrane is sealed to separately close the liquid inlet and the gas inlet. As a result, the liquid inlet can be opened, e.g., by piercing by a liquid injector, while the gas inlet remains closed by the membrane. The gas inlet can be selectively opened, e.g., by piercing the membrane in the gas sealing region of the membrane such as by inserting a needle or lance through the gas inlet.

The capsule of the invention preferably comprises a liquid product delivery system downstream of the first compartment which can be closed or opened before insertion in the liquid supply device. The liquid product delivery system can be configured to maintain a certain liquid pressure (e.g., 2-10 bars) in the compartment which favours dissolution/dispersion of the ingredients with the injected liquid.

For instance, the liquid product delivery system is chosen amongst any one of:
- a perforable or breakable wall,
- a combination of a perforable wall and at least one perforating element,
- a valve comprising at least one hole or slit opening under pressure and,
- a filtering wall with premade orifices for separating the delivered liquid product from solids in the compartment.

The nutritional ingredients contained in the compartment can be under the form of a liquid concentrate, paste, powder and combinations thereof.

The nutritional ingredients preferably comprises an infant formula, a dairy based ingredients, a culinary composition or any other suitable nutritional food including proteins, lipids, carbohydrates, micronutrients, fibres and combinations thereof.

In another independent important aspect, the invention relates to a filter device comprising a filter membrane and an outlet wall for supporting the filter membrane; the outlet wall comprising a liquid inlet and outlet nozzle with at least one liquid outlet; wherein the filter device is configured as a unit for being placed upstream the ingredient's compartment of a capsule for the preparation of a nutritional product; with its nozzle protruding inside the said compartment. In a mode, the liquid outlet of the filter unit is offset to an extent that it is placed outside the axial projection of the filtering surface of the filter membrane.

All the characteristics described in relation to the filter unit are here applicable to the filter device. For instance, filter unit preferably comprises a pressure resistant, handleable, relatively rigid casing comprising liquid inlet and outlets. More preferably, the device comprises a gas inlet for emptying the liquid content capsule which is independent from the liquid inlet and which bypasses the filter membrane. The filter unit can also be provided with an independent gas outlet or, alternatively, the gas outlet is common with the liquid outlet at the nozzle.

BRIEF DESCRIPTION OF THE DRAWINGS

The appended drawings are given as a matter of illustration of the best modes.

DETAILED DESCRIPTION OF THE INVENTION

Figure 1:
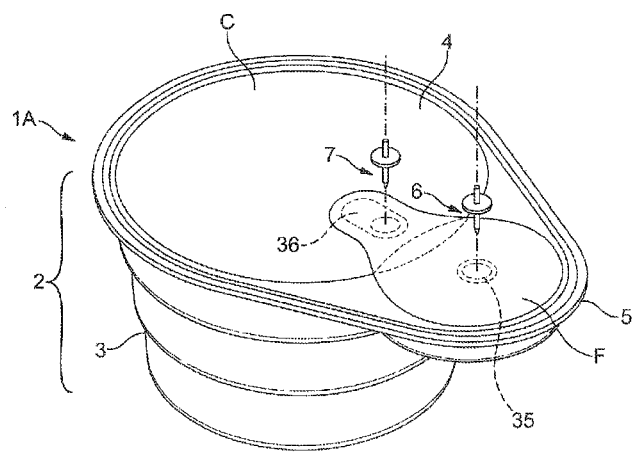
FIG. 1 is a perspective top view of a capsule according to preferred mode of the invention.
Figure 2:
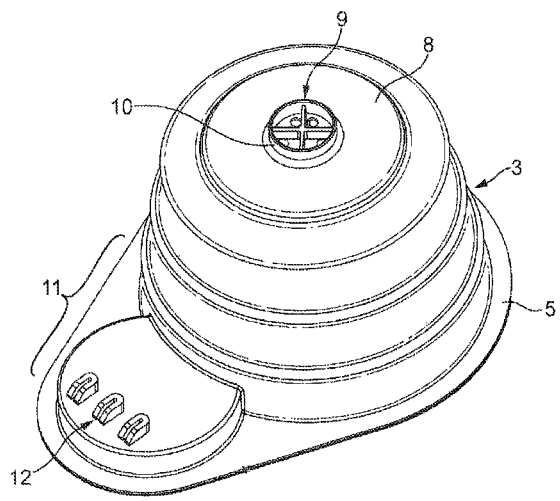
FIG. 2 is a perspective bottom view of the capsule of FIG. 1.
Figure 3:
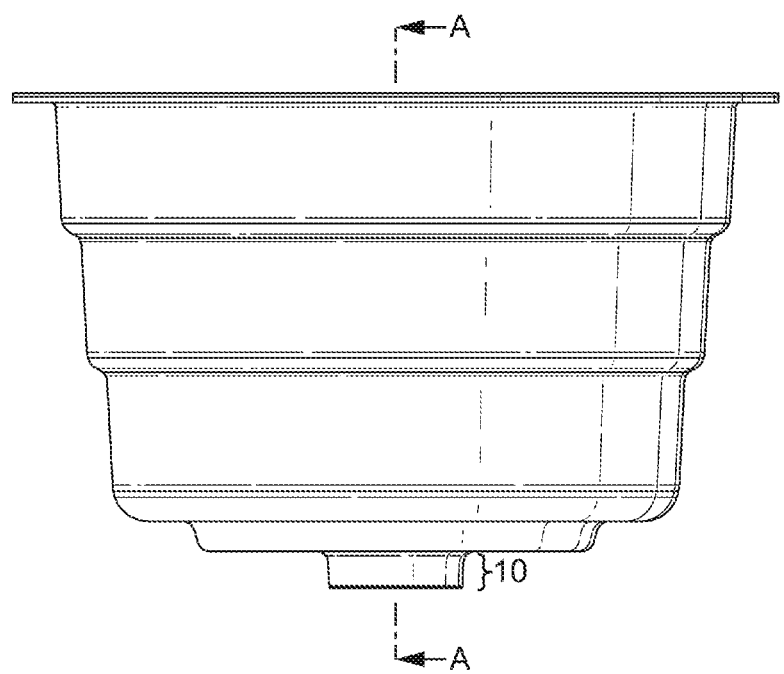
FIG. 3 is a side view of the capsule of FIG. 1.

The general aspect of the capsule according to a first mode of the invention is illustrated in connection with FIGS. 1 to 3 given as a preferred example only. The capsule 1A generally comprises a body 2 for receiving nutritional ingredients, a filter technology and a product delivery technology as will be discussed later on. The capsule has a cup 3 formed in the body which is closed by a liquid impermeable top membrane or foil 4 which is sealed onto the flange like rim 5 of the body. The membrane 4 may be simply liquid impervious or, most preferably, liquid and gas impervious. In particular, the membrane can be a multilayer comprising a gas barrier such as EVOH and/or aluminium. As will be explained in more detail later on, the top membrane is made of a puncturable material such as thin polymer and/or aluminium to enable liquid to be supplied by means of a liquid injector 6 on one hand, and gas to be supplied in the capsule by means of a gas injector 7 on the other hand.

The bottom 8 of the cup 3 comprises a product outlet 9 intended for the release of the liquid nutritional composition/product from the capsule. The product outlet 9 may comprise one or several openings for streaming of the liquid composition towards a receptacle such as a baby bottle, glass or cup. The product outlet 9 may extend from the cup bottom by a short duct 10 for directing the flow of liquid and reducing side projections of liquid which could contaminate the surroundings of the receptacle.

The body of the capsule extends on the upper side by an extension portion 11 which receives the filter for filtering liquid supplied to the capsule. As illustrated on FIG. 2, the capsule may further comprises a three-dimensional coding structure 12 capable of co-acting with positioning sensors of the liquid supply device, for discriminating the type of the capsule inserted in the device so that the preparation cycle may be tailored to the recognized capsule type, e.g., by supplying the proper volume of liquid, varying temperature, flow rate, etc.

Figure 4:
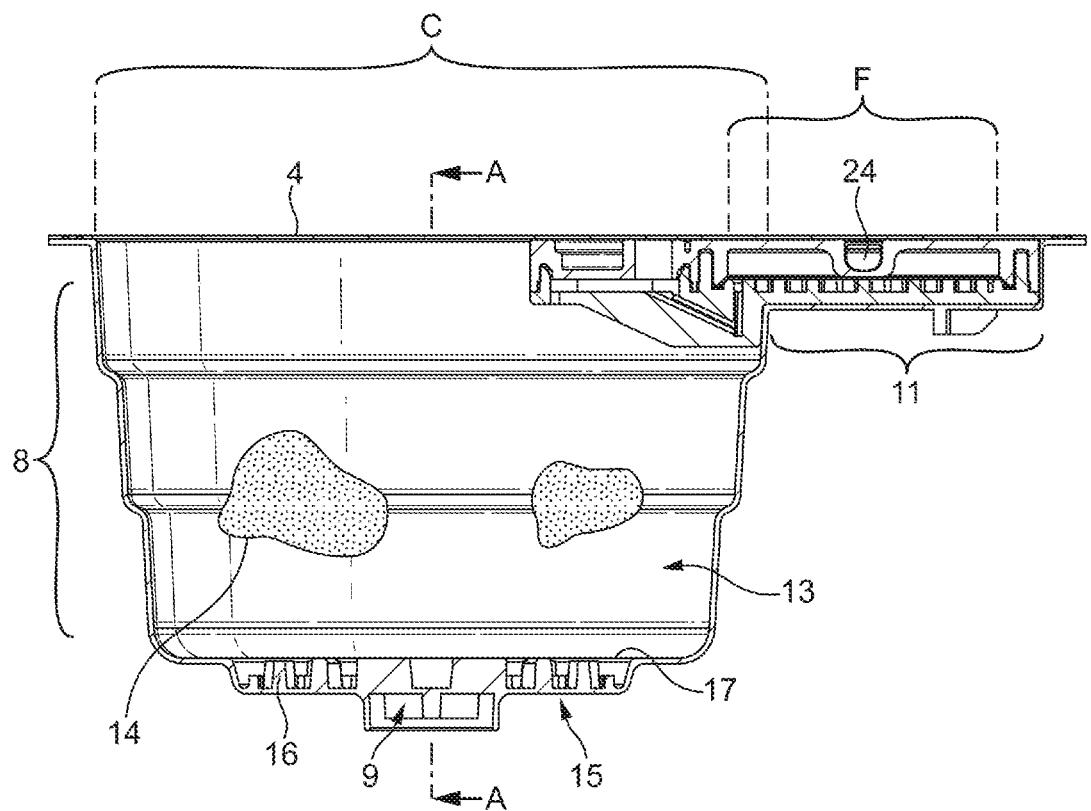
FIG. 4 is cross section of the capsule of FIG. 3 along line A.
Figure 5:
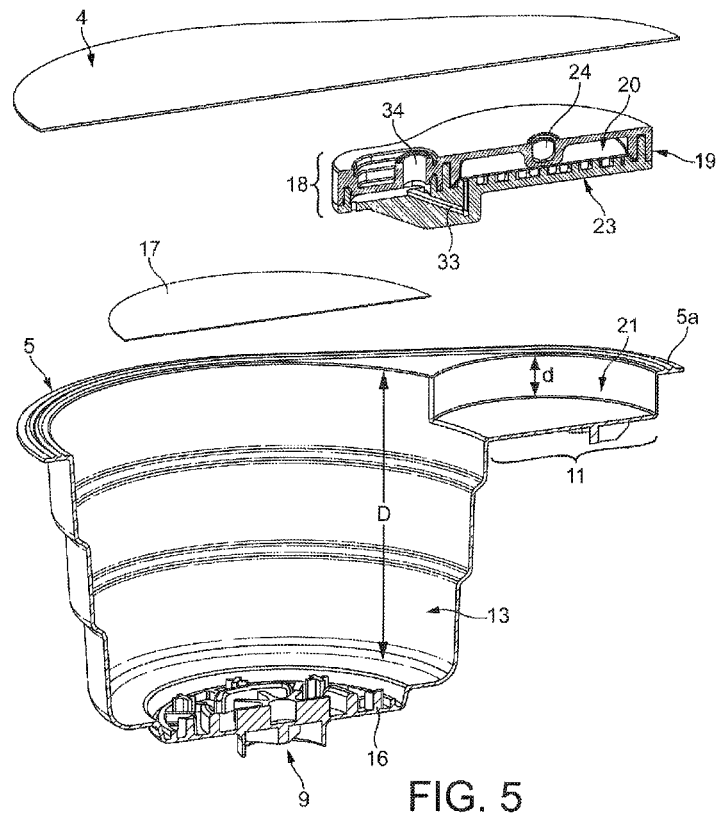
FIG. 5 is an exploded cross sectional view of the capsule of FIG. 1 showing the different elements before assembly.
Figure 6:
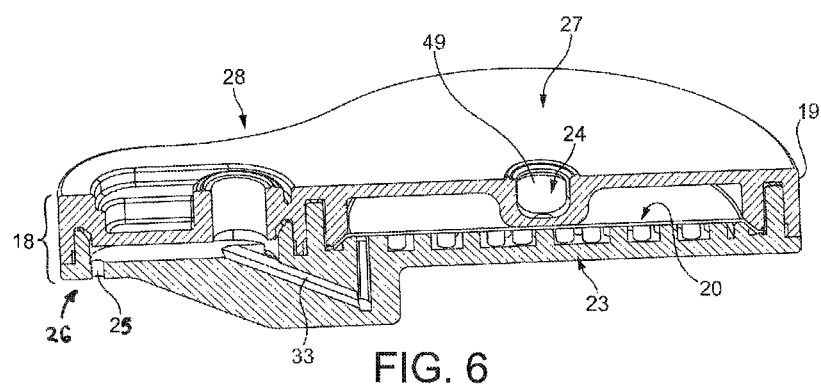
FIG. 6 is an enlarged perspective and cross sectional view of the filter unit of the capsule of FIG. 1.

In view of FIGS. 4 and 5, the capsule comprises, in the cup, a compartment 13 containing nutritional ingredients 14 formed by the bottom and sidewall of the cup 3. The volume of the compartment may vary depending on the volume of liquid to be injected in. In general, a large volume is preferred for large volume of liquid so that the compartment serves as a mixing bowl for the ingredients and liquid to form the composition.

The capsule may comprise a product delivery system 15 for ensuring a proper interaction of the supplied liquid and the ingredients contained in the compartment of the capsule and for reducing, preferably avoiding, contact of nutritional liquid with the device. In a particular mode, the product delivery system is designed to open at least one orifice through the capsule for delivery of the composition when a sufficient pressure of liquid has been reached in the compartment. For this, the bottom 8 of the cup comprises perforating elements 16 strategically placed to perforate a lower membrane 17 normally separating the compartment 13 from the liquid product outlet 9. The lower membrane is typically a thin liquid-tight perforable membrane made of aluminium and/or polymer. The membrane is sealed at the bottom edge of the cup. For instance, the membrane is a 30-micron foil of aluminium. A capsule comprising such a product delivery system is described in PCT/EP09/053,033 filed on 16 Mar. 2009 which is incorporated here by reference. It should be noted that the product delivery system can be designed differently. For instance, it can be a simple valve comprising an orifice or slot normally closed and which opens under the pressure which builds in the compartment as resulting from the liquid being supplied in. In another alternative, it can also be a porous wall forming a product filter.

The capsule of the invention is further designed to ensure filtration of the liquid being supplied in the compartment. The rationale for filtration of incoming liquid is essentially linked to the requirement for controlling a perfect quality of the liquid, e.g., water, entering in the delivered composition. Water can be supplied at a temperature of service, e.g., at about 35-40 degrees Celsius, by heating of ambient water coming from a water tank of the fluid supply device. More preferably, the filtration is carried out to remove contaminants including microorganisms such as bacteria, yeast or molds and eventually viruses, e.g., which have not been destroyed by the water heating operation. For this, a solution can consists in inserting, in a predetermined area of the capsule, a filter unit 18 in the form of a pressure resistant, handleable unit comprising an outer protective casing 19 and at least one filter media, in particular, a filter membrane 20. The filter unit 18 is preferably rigid in the sense that it is more rigid than the filter membrane and preferably, it is also resistant to significant deflection upon application of the liquid and sealing pressure exerted by the liquid coming out of the injector and by the sealing engagement of the fluid supply device itself onto the capsule. The filter unit presents the advantage to facilitate the placing of the filter technology in the capsule, without requiring specific connection means, and it reduces the risk of damaging the filter membrane.

For antimicrobial purpose, the filter membrane has preferably a pore size of less than 0.4 microns, most preferably of less than 0.2 microns. It may have a thickness of less than 500 microns, preferably between 10 and 300 microns. The material of the membrane can be chosen from the list consisting of PES (polyethersulfone), cellulose acetate, cellulose nitrate, polyamide and combinations thereof.

In particular, the filter unit is insertable in a filter receiving seat 21 formed at the extension portion 11 of the body. In a preferred embodiment, the filter receiving seat 21 extends by a flange-like rim 5a which merges continuously with the flange-like rim 5 of the body 2. The filter receiving seat is so designed to position the filter unit in an offcentred manner relative to the compartment. As a result, the deformation of the capsule due to the pressure of liquid and the sealing with the device can be reduced compared to a more central positioning above the compartment. The filter receiving seat 21 may be, for instance, a u-shaped cavity of relatively low depth (d) compared to the depth (d) of the compartment. The seat 21 has a bottom wall and a sidewall matching at least part of the bottom and sidewall of the filter unit, in particular, of its larger portion 27. The filter unit may not require any specific connection with the filter receiving seat but it is simply maintained in place by the complementary shapes of the unit, e.g., by press-fitting, in the seat and the closure obtained by the top membrane 4. For instance, the seat 21 may comprise corrugations or recesses in its sidewall, e.g., near the compartment, for receiving the filter unit by press-fitting (not shown).

As illustrated in FIG. 4, the filter unit 18 is sized so that its filtering surface (F) is at least two times, preferably several times smaller than the larger cross section (C) of the mouth (i.e., upper opening) of the compartment 13, e.g., corresponding to the upper opening of compartment. Furthermore, the largest portion of filtering surface (F) is axially offset relative to the cross section (C) of the compartment (13) when the capsule is viewed in projection view along axial line A. By "largest portion", it is meant that at least 60%, preferably 85% of the filtering surface is placed outside the cross section of the compartment in the projection along direction A. The filtering surface is here considered as the total surface of the filter membrane minus its pinched circumference 30. A certain overlap of the surfaces may be considered as acceptable. A first problem solved is the reduction of the compartment and the ability to better control the deformation of the filter. Another problem solved is about the reduction of the amount of material for the filter membrane and consequently the reduction of the manufacturing cost and the impact of the used capsule on environment. Another advantage is the possibility to compress the capsule, in particular, the cup of the capsule after emptying for reducing the storage volume of the used capsules. For this, the capsule may be provided with a sidewall including weakened lines oriented in such as way to promote compression of the cup in the axial direction.

As illustrated in FIGS. 6 to 9, the filter unit of the invention comprises an inlet wall 22 for introduction of liquid in the unit and an outlet wall 23 for delivery of filtered liquid in the compartment 13. The inlet wall comprises a liquid inlet 24 whereas the outlet wall comprises a liquid outlet 25 formed at a nozzle 26 of the unit. The liquid inlet and outlets 24, 25 are spaced apart in the axial direction so that liquid inlet 24 is placed outside the contour of the compartment 13 whereas the outlet 25 is placed inside the contour of the compartment. As a matter of preferred design, the filter casing can take the form of a racket with a larger portion 27 positioned in the seat and extending by a narrowing portion 28 which extends transversally above the compartment. The outlet 25 preferably has a small diameter, e.g., between 0.2 and than 1.5 mm, to form a jet of liquid under pressure that promotes dissolution and/or dispersion of the ingredients by liquid projected through the nozzle. The outlet may be formed of several discrete openings. The number of openings should be small, preferably between 1 and 5 at maximum to avoid a too large reduction of the flow velocity. In a mode, two parallel or non-parallel outlets are provided in the nozzle. The flow velocity through the outlet(s) of the nozzle is preferably comprised between 1 and 20 msec. The outlet can have different cross section such as circular, oval, rectangular, etc.

The casing encloses the filter membrane 20 in an inner compartment 29 forming an upstream side and downstream side with the circumference 30 of the filter being sealed by the casing in a liquid-tight manner so to avoid bypass of the filter by liquid. At the downstream side of the compartment, the filter membrane is further supported by a support structure formed, e.g., of a multitude of small studs 31. The studs have flat free ends to reduce axial deflection of the filter membrane under pressure and avoid its breakage. The studs are preferably formed along the whole cross section of the filter membrane. More preferably, adjacent studs are not distanced of more than 2.5 mm. Between the support structure is formed a multitude of channels 32 for collecting the liquid being filtered through the membrane. The outlet wall 23 comprises at least one outlet conduit 33 for making fluid communication between the downstream side of the filter membrane, via channels 32, and the outlet 25 of nozzle 26. The support structure can be a separate element, e.g., a grid placed in the casing below the filter.

At the inlet wall 22, the filter unit further comprises a gas inlet 34 for enabling supply of gas under pressure, e.g., compressed air, in the compartment 13. The gas inlet can be, as illustrated, an opening through the wall intersecting with the outlet conduit 33. Therefore, it should be noted that gas entering the unit will bypass the filter membrane 20 on its way to the nozzle 26 and will enter under pressure the compartment. As a result, the filter membrane does not create a pressure loss for the gas before entering the ingredient's compartment. Both the liquid inlet 24 and the gas inlet 34 are closed by the top membrane 4. Hence, the inlets are selectively openable by perforating the membrane 4 at the dedicated inlets. In particular, the top membrane 4 is sealed around the liquid inlet and gas inlet by seals 35, 36 (FIG. 1). Therefore, when the top membrane is perforated by the gas injector 7 of the fluid supply device, the tip of the perforator can only enter in contact with filtered liquid. As a result, there is a much lower chance of contamination of the perforator than if the gas and liquid inlet were the same entry. The gas perforator can so remain clean for the next preparation cycle.

Figure 7:
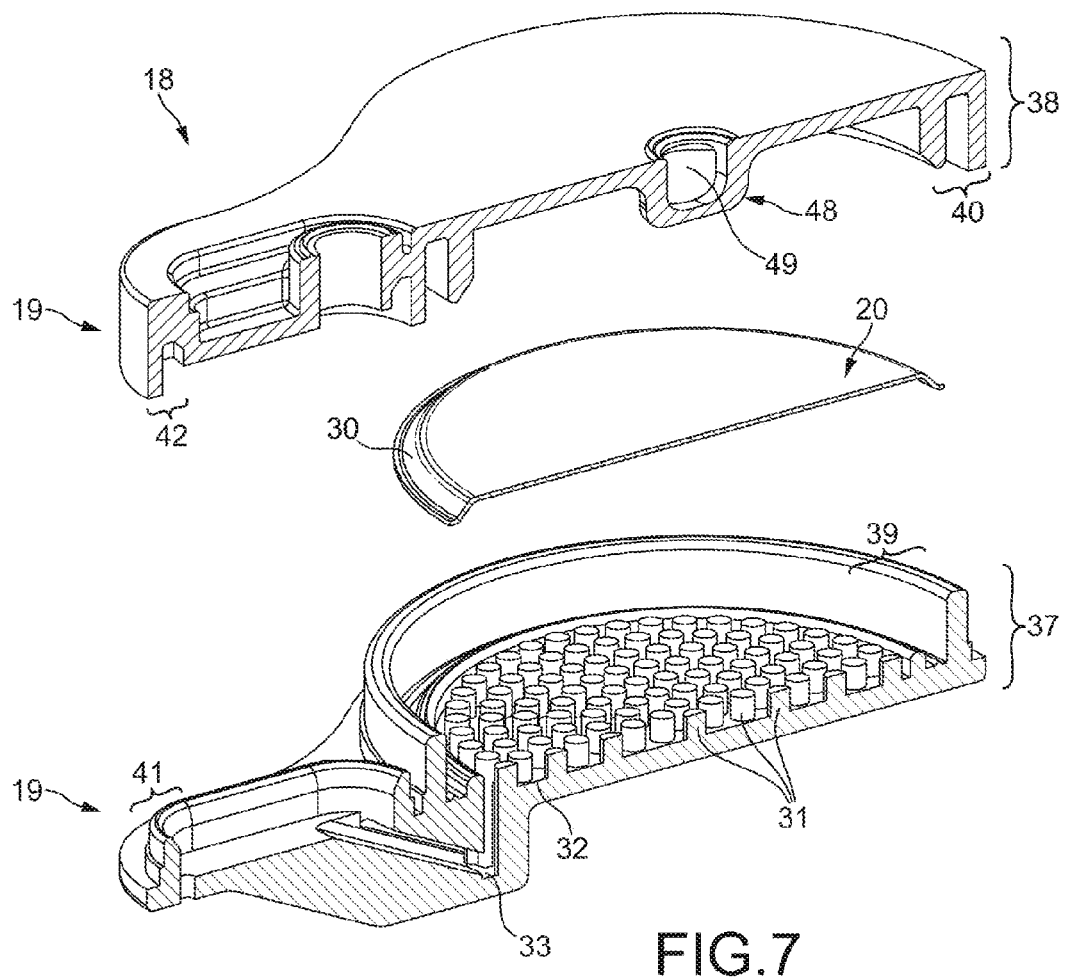
FIG. 7 is an exploded view of the filter unit of FIG. 6.

The structure of the filter casing 19 can vary. However, in a preferred design, the casing is formed of two parts 37, 38 which are welded and/or clipped together. FIG. 7 shows the filter unit 18 with a lower half casing 37 and an upper half casing 38. The lower half casing 37 has a protruding circular ridge/groove section 39 which delimits the contour of the inner compartment for fitting in a circular groove/ridge section 40 of the upper half casing 38. Similarly, the narrowing portion 28 of the unit is assembled by a second ridge/recess section 41 in the lower half casing that fits into a groove/ridge section 42 of the upper half casing 38. It could be as well that sections 39, 41, respectively 40, 42 form continuous sections from the larger portion 27 of the racket to the narrowing portion 28 of the racket.

Figures 10, 11:
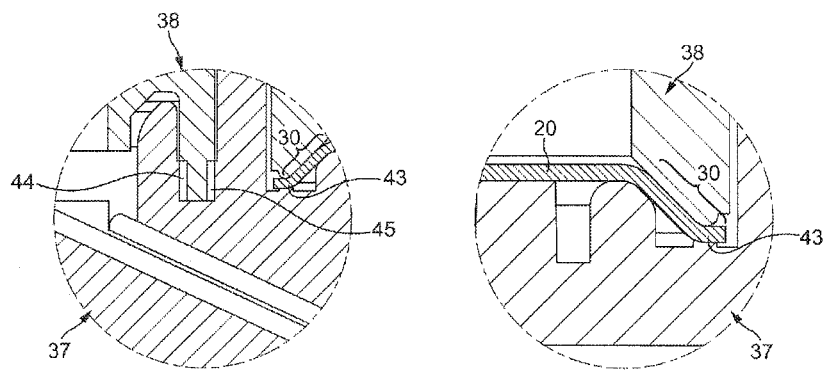
FIG. 10 is a detail in cross section of the welded assembly of the filter unit of FIG. 6.
FIG. 11 is another detail in cross section of the filter membrane connection in the casing of the filter unit.

As illustrated in FIGS. 10 and 11, the lower and upper half casings 37, 38 are assembled while pinching the circumference 30 of the filter membrane. The parts 37, 38 can be designed in such a way to bend the circumference and pinch it at a circular point 43. The filter might not be necessary welded to the casing if the pinch point is sufficient to maintain the filter firmly in place and therefore successfully avoid bypass effect during operation. The unit can thus be assembled by welding at the groove/ridge sections by suitable welding lines 44, 45 for instance. The benefit of welding the casing parts but pinching the filter resides in the possibility to choose amongst a larger material choice for the filter without having to care for welding compatibility with the material of the casing. Another benefit is to simplify assembly by using ultrasonic welding for the thicker elements of the unit and avoid damaging the thinner element (i.e., filter membrane).

Figure 8:
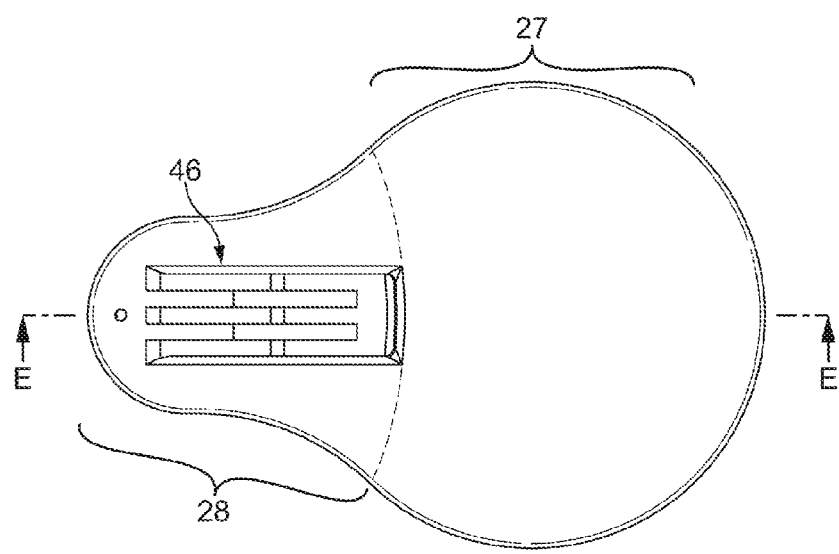
FIG. 8 is a bottom plane view of the filter unit of FIG. 6.
Figure 9:
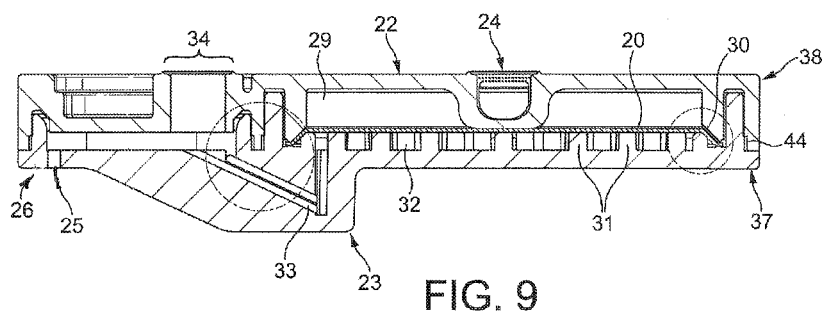
FIG. 9 is an enlarged plane cross sectional view of the filter unit of FIG. 8 along line E.

As shown in FIG. 8, the structure of the filter unit may be optimized. For example, the filter unit can comprise a reinforcing structure 46, in particular, at the narrowing portion 28 to enable the conduit to be formed in the lower wall but while still maintaining rigidity of the unit, in particular, in view of fluidic and/or mechanical constraints. For instance, the reinforcing structure forms a series of ribs extending, for instance, in the transversal direction of the racket. Of course, many different reinforcing patterns are possible. In particular, the ratio rigidity-to-weight should be optimized to promote cost reduction and lower impact on environment.

Figure 12:
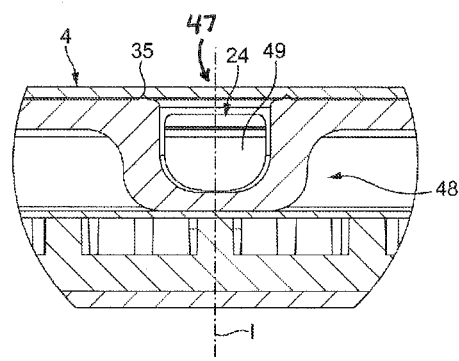
FIG. 12 shows another detail in cross section of the inlet of the filter unit.

In order to reduce the risk of damaging the filter membrane during opening of the liquid inlet 24 when perforating the membrane 4 in the area 47 just above the inlet, as illustrated in FIG. 12, a perforation-resistant deflector 48 is provided between the inlet and the filter membrane 20. The deflector 48 can be made integral with the inlet wall of the casing. It can be designed as a transversal bridge crossing the inlet opening and inset relative to the opening. Therefore liquid may pass by side passages 49 formed in the inlet between the bridge and the wall. Of course, the deflector could take various forms provided it creates a protection against perforation along inlet axial direction I. The deflector could also be a separate piece interposed between the filter and the inlet wall.

Figure 13:
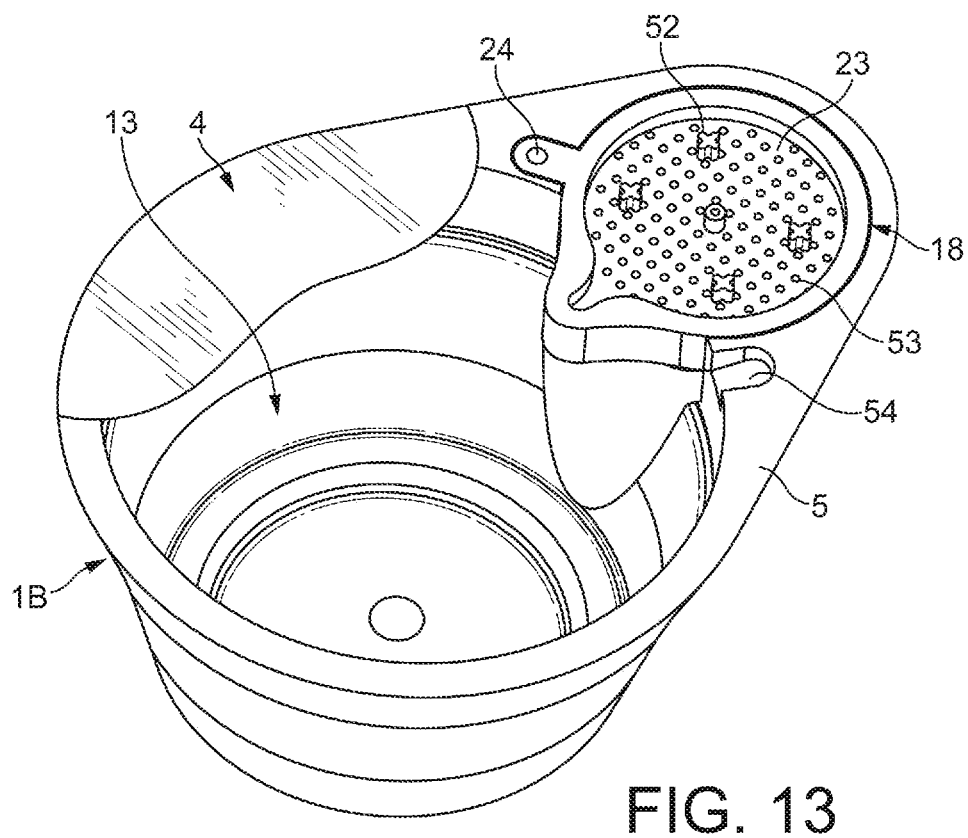
FIG. 13 shows, in top perspective view, a second embodiment of the capsule of the present invention with the top membrane being removed for clarity.
Figure 14:
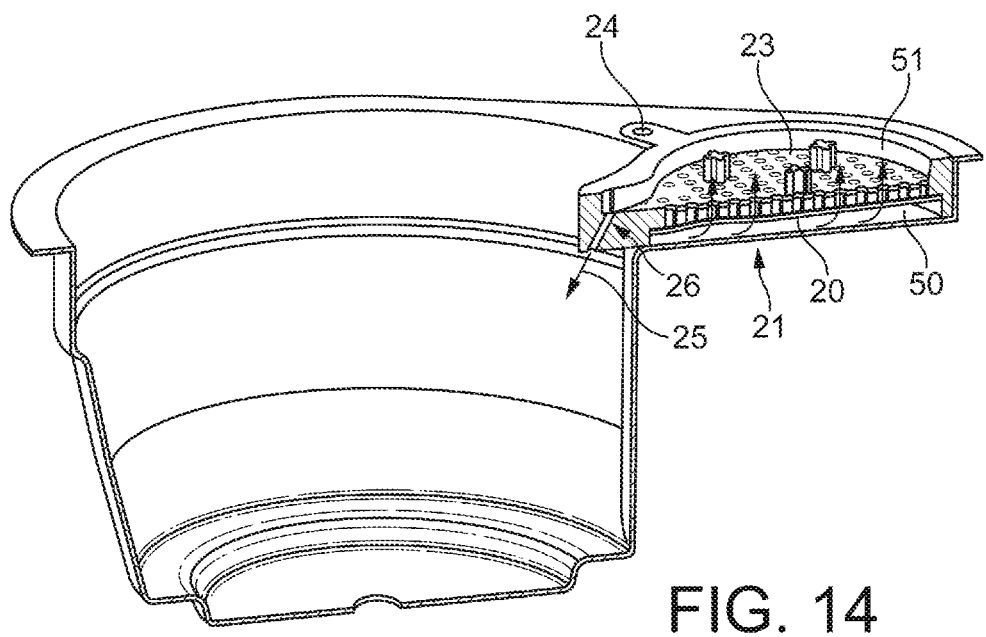
FIG. 14 shows in cross section perspective view the capsule of FIG. 13.
Figure 15:
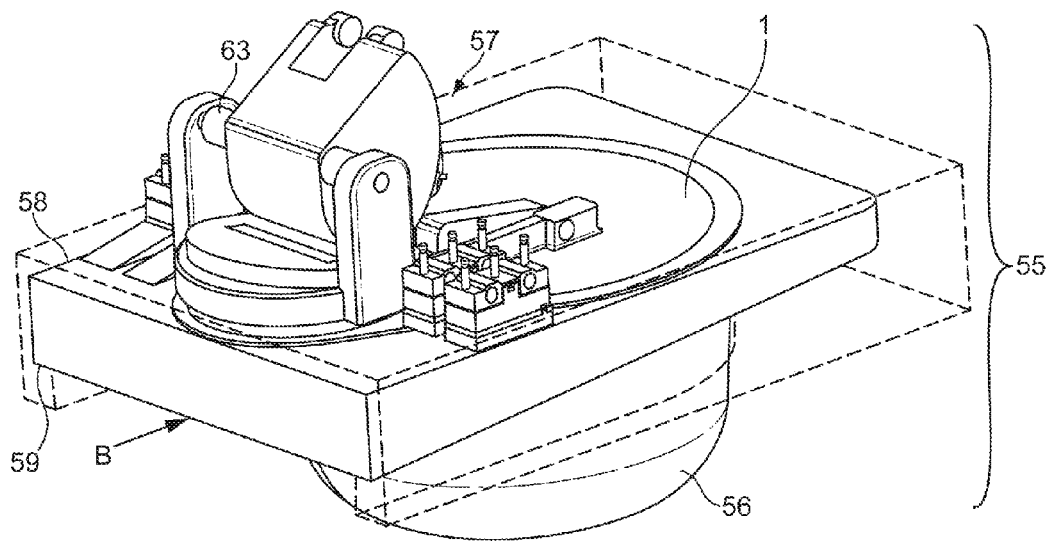
FIG. 15 shows a perspective view of a fluid supply device of the invention in which is inserted a capsule of the invention before opening of the liquid inlet for supply of liquid in the capsule.
Figure 16:
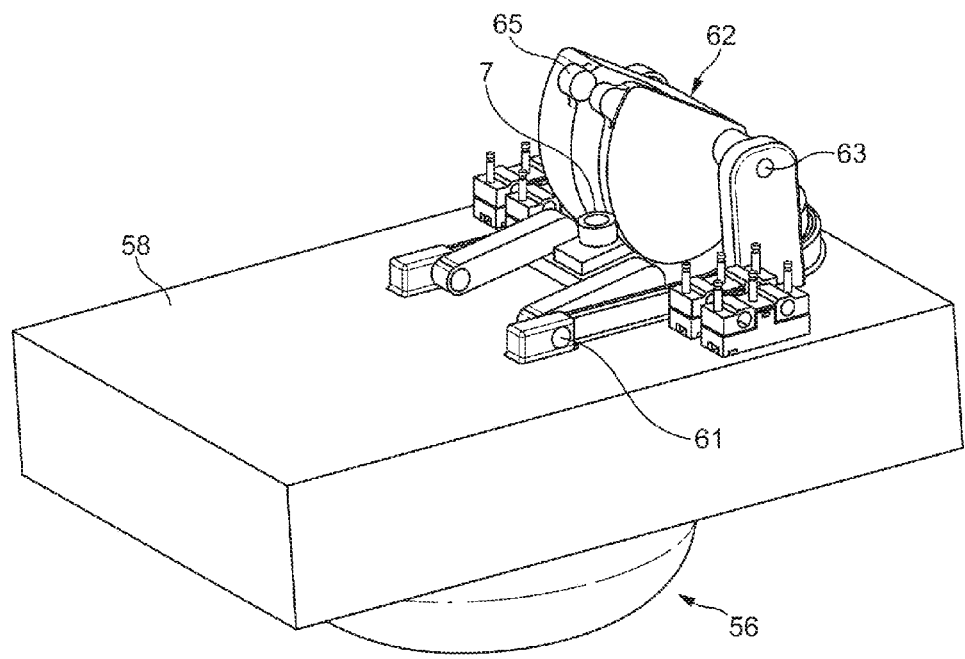
FIG. 16 shows a perspective view from a different angle of the fluid supply device of the invention still before opening of the liquid inlet.

In another embodiment illustrated in FIGS. 13 and 14, the capsule 1B of the invention differs in different aspects. First of all, a filter unit 18 is provided which comprises an outlet wall 23 onto which is applied the filter membrane 20. Contrary to the previous embodiment, the filter membrane 20 is placed between the outlet wall 23 and the bottom of the filter receiving seat 21 of the body. A liquid inlet 24 is provided on the side of the unit which communicates with the lower compartment 50 placed upstream of the filter but below the outlet wall 23. A second upper compartment 51 is formed between the outlet wall 23 and the top membrane (not shown) 4 which is sealed on the flange-like rim 5 of the body of the capsule. In order to avoid the top membrane 4 from collapsing in the upper compartment 51 and partially blocking the flow coming out of the filter membrane, the outlet wall 23 of the filter is provided with several support elements 52. The outlet wall is further provided with a multitude of openings 53 for allowing filtered liquid to properly distribute through the filter membrane placed upstream. Therefore, the liquid supplied in the capsule through liquid inlet 24 flows under the unit in the lower compartment 50 then through the filter membrane 20 in the upward direction. The filtered liquid is thus collected in the upper compartment and flows through the outlet nozzle 26 comprising a small-size outlet 25. For emptying capsule 1B, a gas inlet can be provided independently from the filter unit. In particular, an indentation 54 can be formed in the flange like rim, e.g., beside the filter unit. For gas to be supplied in the ingredients compartment 13, the top membrane is perforated at the site of the indentation. Perforation of the membrane can be carried out by a mechanical element of the fluid supply device or by gas under pressure. Of course, the gas inlet could also be provided in the filter unit. The product delivery system can be the same as described in the first mode.

The description will now be focused, in relation to FIGS. 15 to 20, on the fluid supply device according to the invention adapted for receiving a capsule for preparation of a nutritional composition as described.

The fluid supply device 55 of the invention typically comprises a capsule holder 56 adapted in size to receive the capsule 1. The capsule holder fits with a fluid supply group 57 comprising liquid and gas supply means. The fluid supply group 57 comprises a capsule holder insertion base 58 for offering a stable position of reference for the capsule holder. In particular, complementary guiding means 59 on the capsule holder 56 and base 58 are provided for enabling easy assembling and removal of the capsule holder from the base such as along a longitudinal sliding direction B.

It should be noted that the filter unit 18 of the invention could as well be a separate part which is associated with the capsule at the time of use, e.g., during insertion of the capsule in the fluid supply device. For instance, the filter unit can be part which is associated to the liquid injector or integrated in the liquid injector.

Figure 17:
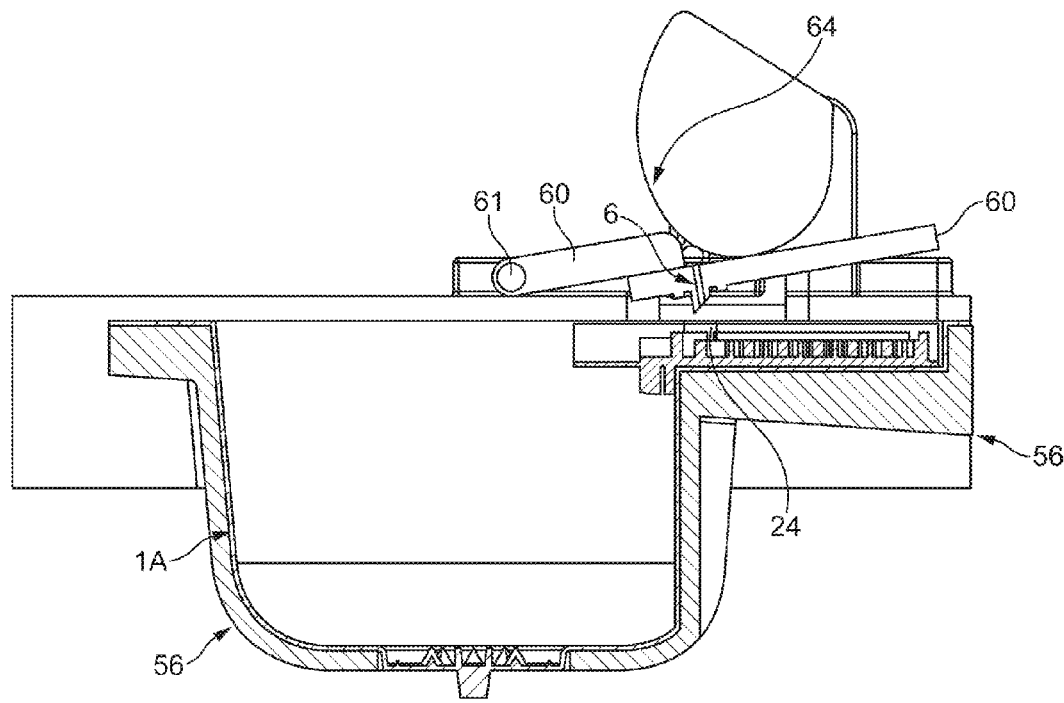
FIG. 17 is a cross sectional view of the device of FIG. 15 along a plane passing through the liquid injector still before opening of the liquid inlet.
Figure 18:
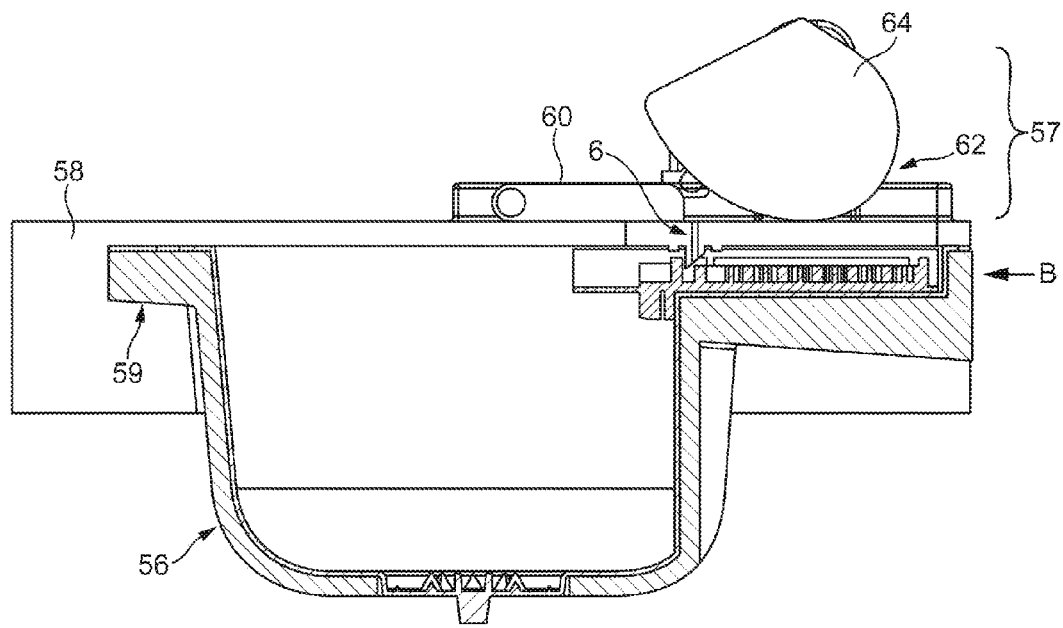
FIG. 18 is a cross sectional view of the device of FIG. 15 along a plane passing through the liquid injector still after opening of the liquid inlet.
Figure 19:
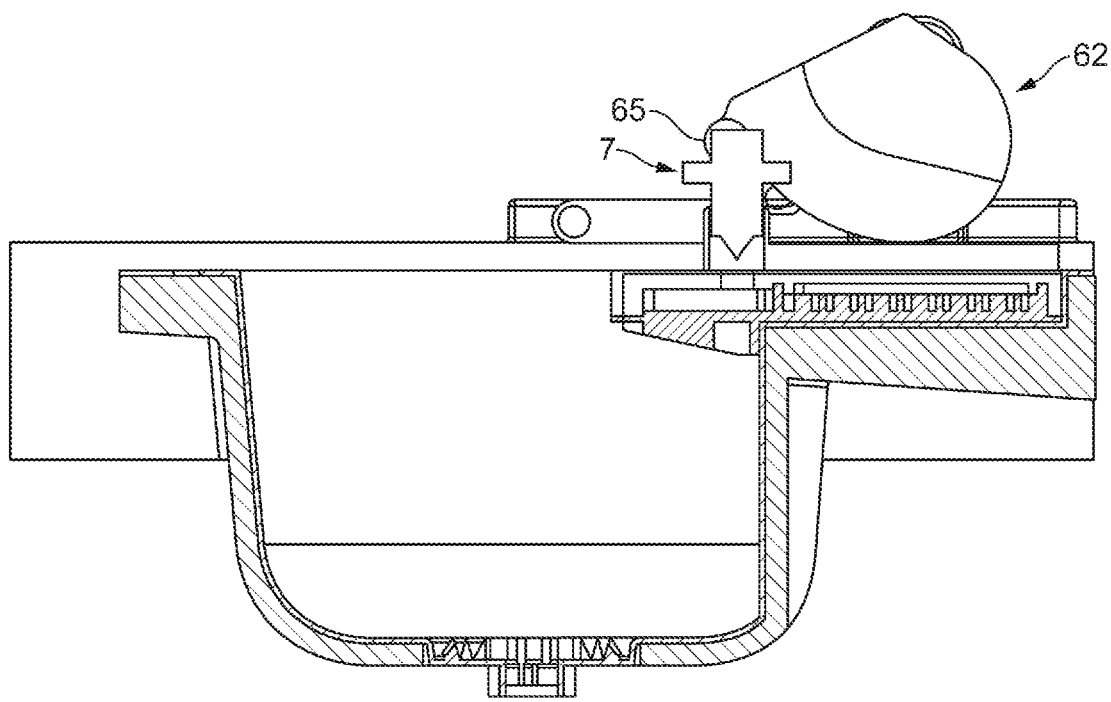
FIG. 19 is a cross sectional view of the device of FIG. 15 along a plane passing through the gas injector before opening of the gas inlet.
Figure 20:
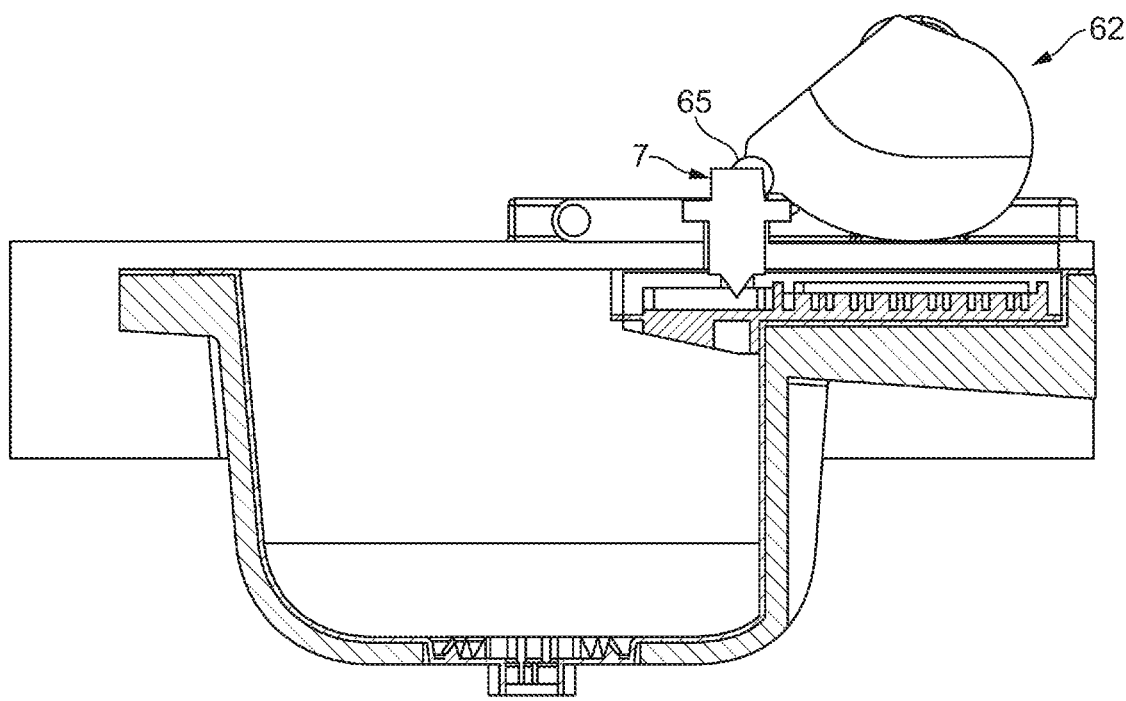
FIG. 20 is a cross sectional view of the device of FIG. 15 along a plane passing through the gas injector after opening of the gas inlet.

The fluid supply group 57 further comprises a liquid injection plate 60 bearing the liquid injector 6 by itself. The liquid injection plate 60 can be positioned to rotate along an axle 61 mounted on the top part of the base 58 such that the plate can take at least a first position at which the injector is placed away from the liquid inlet opening of the capsule and a second position at which the injected is engaged in opening of the liquid inlet 24. The first position is illustrated on FIG. 17 whereas the second position is illustrated in FIG. 18. The injection plate moves from the first position to the second position, and vice versa, by a cam mechanism 62 which is also mounted in rotation along a second axle 63 on the base. Similarly, a gas injector 7 is provided which can take a first position where it maintained away from the gas inlet of the capsule (FIG. 19) and a second position where it is engaged in opening of the gas inlet (FIG. 20). Again the change from first to second position of the gas injector 7 is controlled by the cam mechanism 62. In an advantageous manner, the cam mechanism 62 is common to control both the positions of the liquid and gas injectors in such a manner that the gas injector moves from its first to second position at a time the liquid injector has already moved from first to second position. The cam mechanism 62 in particular comprise at least one first cam portion 64 acting on the injection plate and at least one second cam portion 65 acting on the gas injector. The two cam portions are linked to the same cam mechanism so that they always act on their respective injectors in a coordinated manner. FIGS. 17 and 18 show the first cam portion 64 acting to change the position of the liquid injector 6 by pushing the plate 60. The cam portion 64 forming an eccentric surface relative to axle 63 which pushes the plate 60 downwards in direction of the capsule. It should be noted that sealing means such as an O-ring (not shown) may be associated to the injection plate for locally creating a liquid seal around the liquid inlet. FIGS. 19 and 20 show the second cam portion 65 also forming an eccentric surface pushing on the gas injector 7 in direction of the gas inlet. For clarity, the device does not show all the detail, in particular, the elastic return means for replacing the liquid injection plate in its first position and similar means for replacing the gas injector in its first position. Such elastic return means can be in the form of springs or equivalents.

In a different mode, the filter unit 18 can separate from the capsule and be a disposable device.

What is claimed is:

1. A sealed capsule for the preparation of a nutritional product in a device adapted to supply liquid in the capsule, the capsule comprising:
    a body comprising a bottom end and a sidewall that form an ingredient compartment containing nutritional ingredients for the preparation of the nutritional product in combination with the supplied liquid,
    an extension protruding radially outward from a top end of the sidewall of the body of the capsule and comprising a filter-receiving seat;
    a filter unit comprising a casing that is separate from the body of the capsule and encases a filter adapted for removing contaminants contained in the liquid,
    wherein the filter unit is positioned in the filter receiving seat and comprises a filter membrane and an inlet wall and an outlet wall of the casing which together form a filter compartment for encasing and supporting the filter membrane;
    the inlet wall comprising a liquid inlet port to the filter compartment;
    the outlet wall comprising at least one liquid outlet emerging into the ingredient compartment; and
    wherein at least part of the filtering membrane is offset relative to the ingredient compartment when viewed in a vertically extending axial projection of the capsule such that the liquid inlet port is positioned outside of the ingredient compartment of the capsule and above the extension, with the liquid inlet port and the ingredient compartment on opposite sides of the sidewall relative to each other; and a membrane on top of the capsule, thereby sealing the capsule.

2. The capsule according to claim 1, wherein the filter membrane and the liquid outlet each have a central vertical axis, the central vertical axis of the liquid outlet is positioned axially offset relative to the central vertical axis of the filter membrane, and the central vertical axis of the filter membrane is positioned outside of the ingredient compartment of the capsule.

3. The capsule according to claim 1, wherein the filter membrane is a micro-porous membrane.

4. The capsule according to claim 1, wherein the filter-receiving seat comprises surfaces complementary to surfaces of the casing.

5. The capsule according to claim 1, wherein the filter membrane is liquid imperviously sealed to the casing at a peripheral portion of the filter membrane.

6. The capsule according to claim 1, wherein the casing is formed of two half casings which are joined together and which hold the filter membrane at a periphery of the filter membrane.

7. The capsule according to claim 1, wherein the liquid inlet port has a central vertical axis and includes at least one perforation-resistant deflector traversing the central vertical axis of the liquid inlet port for preventing perforation of the microporous membrane by a liquid injector of the fluid supply device, and the central vertical axis of the liquid inlet port is positioned outside of the ingredient compartment of the capsule.

8. The capsule according to claim 1, further comprising a plurality of ridges or studs or a grid positioned between the outlet wall and the filter membrane for supporting the filter membrane and for reserving space for the filtered liquid.

9. The capsule according to claim 1, wherein the filter-receiving seat is upstream of the ingredient compartment for lodging the filter unit in the capsule.

10. The capsule according to claim 9, wherein the filter unit comprises a largest portion positioned in the filter receiving seat and a narrowing portion forming the liquid outlet.

11. The capsule according to claim 9, wherein the filter-receiving seat is placed transversally offcentered relative to the ingredient compartment such that the filter-receiving seat and the ingredient compartment are positioned on opposite sides of the sidewall of the capsule relative to each other.

12. The capsule according to claim 11, wherein the filter-receiving seat extends by a flange-like rim which merges continuously with a corresponding flange-like rim of the ingredient compartment.

13. The capsule according to claim 1, further comprising an openable gas inlet arranged to bypass the filter membrane and to provide communication between the exterior of the capsule and the interior of the ingredient compartment.

14. The capsule according to claim 1, wherein a common top membrane is sealed onto both the ingredient compartment and the filter unit.

15. The capsule according to claim 1, further comprising a liquid product delivery system downstream of the ingredient compartment wherein the delivery system is in the form of one of a perforable or breakable wall, a combination of a perforable wall and at least one perforating element, a valve comprising at least one hole or slit that is constructed to open under pressure, and a filtering wall with premade orifices for separating the delivered liquid product from solids in the ingredient compartment.

* * * * *